US006187265B1

United States Patent
Wu et al.

(10) Patent No.: US 6,187,265 B1
(45) Date of Patent: Feb. 13, 2001

(54) APPARATUS AND METHOD TO DELIVER STERILANTS TO ARTICLES HAVING CONTACT SURFACES

(75) Inventors: Su-Syin S. Wu, Irvine; Nancy S. Chu, Laguna Niguel, both of CA (US)

(73) Assignee: Johnson & Johnson Medical, Inc., New Brunswick, NJ (US)

( * ) Notice: Under 35 U.S.C. 154(b), the term of this patent shall be extended for 0 days.

(21) Appl. No.: 09/384,761

(22) Filed: Aug. 27, 1999

Related U.S. Application Data

(63) Continuation of application No. 08/992,131, filed on Dec. 17, 1997, now abandoned.

(51) Int. Cl.$^7$ ................................................ A61L 2/20
(52) U.S. Cl. ............................ 422/28; 422/292; 422/295; 422/300
(58) Field of Search ............................. 422/28, 292, 295, 422/300

(56) References Cited

U.S. PATENT DOCUMENTS

| | | | |
|---|---|---|---|
| 5,269,790 | * 12/1993 | Funatsu | 606/142 |
| 5,492,671 | * 2/1996 | Krafft | 422/26 |
| 5,552,115 | * 9/1996 | Malchesky | 422/28 |
| 5,580,530 | * 12/1996 | Kowatsch et al. | 422/292 X |

FOREIGN PATENT DOCUMENTS 58-180130 * 10/1983 (JP) .

* cited by examiner

Primary Examiner—Jill Warden
(74) Attorney, Agent, or Firm—Knobbe, Martens, Olson & Bear, LLP

(57) ABSTRACT

An apparatus and method for sterilizing devices having contact areas with an antimicrobial fluid such as hydrogen peroxide. If the device is a lumen, the lumen is held in an adaptor which is connected with a vessel containing the antimicrobial fluid. The lumen, adaptor, and vessel containing the antimicrobial fluid are placed in a sterilization chamber. When the sterilization chamber is evacuated, the antimicrobial fluid in the vessel volatilizes, thereby sterilizing the interior of the lumen. The adaptor has one or more features which improve the sterilization of the areas of contact between the adaptor and the lumen. 1. The surface of the adaptor which is in contact with the lumen can be textured or uneven so as to reduce surface contact and enhance bidirectional diffusion of the sterilant. 2. The adaptor can be made of a material which has minimal chemical and physical interaction with the sterilant. 3. The material from which the adaptor is prepared can be permeable to the sterilant so that the sterilant can penetrate the adaptor to sterilize any areas of contact. These features can be used singly or in combination to improve the sterilization of the areas of contact. These modifications can also be applied to any holder for equipment to be sterilized or to a medical device made of two or more pieces where there are contact areas between the parts, such as forceps.

24 Claims, 2 Drawing Sheets

APPARATUS AND METHOD TO DELIVER STERILANTS TO ARTICLES HAVING CONTACT SURFACES

This application is a continuation of Ser. No. 08/992,131 filed Dec. 17, 1997, abandoned.

FIELD OF THE INVENTION

The invention relates to the sterilization of articles such as medical instruments having long narrow lumens, and, more particularly, to an apparatus and method for delivering an antimicrobial fluid more effectively to contact surfaces within an instrument or between an instrument and the device which holds it during the sterilization process.

BACKGROUND OF THE INVENTION

Articles such as medical instruments should be sterilized before use. There are many methods of sterilization, including heat and chemical methods. Heat sterilization is normally done using steam. Some equipment cannot withstand either the heat or the moisture from steam treatment. As a result, chemical sterilization is now commonly used.

Chemical sterilization uses a sterilizing fluid such as hydrogen peroxide, ethylene oxide, chlorine dioxide, peracetic acid, or a combination thereof. A plasma may be induced to enhance the sterilization process. Although chemical sterilization is normally highly effective, it may not be as effective with medical devices containing long, narrow tubes, or lumens. Sterilization of these long lumens requires that the sterilizing agent penetrate the entire length of the long narrow tube. It is difficult for the sterilizing agent to completely penetrate these long narrow tubes. In order to enhance the penetration of the sterilizing agent down the entire length of the lumen, several forms of apparatus have been developed to flow sterilizing agent through the length of the lumen, thus enhancing the effectiveness of the sterilizing treatment.

For example, U.S. Pat. Nos. 4,410,492 and 4,337,223 describe a sterilization method in which the lumen is placed in a socket connected to a valve and a recirculating pump. The sterilizing gas is recirculated from the sterilization chamber through the lumen of the instrument. Although the method is effective at sterilizing the lumen, sterilization of endoscopes requires 2–3 hours using ethylene oxide as the sterilizing gas.

A method which delivers sterilizing agent down long, narrow lumens is described in U.S. Pat. No. 5,580,530. The lumen is inserted into an adaptor connected to a vessel containing hydrogen peroxide called the booster. The lumen, adaptor, and booster are all placed in the sterilization chamber. When the sterilization chamber is evacuated during the sterilization procedure, the hydrogen peroxide in the booster vaporizes and passes through the lumen, thereby sterilizing the interior of the lumen.

During use of the various sterilization methods, the lumen is held by a connecting device, a socket in the case of U.S. Pat. Nos. 4,410,492 and 4,337,223 or a truncated cone adaptor when using the method of U.S. Pat. No. 5,580,530. In all cases, there are areas of contact between the device and the lumen where the lumen attaches to the connecting device. It is difficult for the sterilizing agent to penetrate into these contact areas. There is a need for a method of enhancing the penetration of sterilizing gas into these contact areas more effectively to allay any potential concerns about incomplete sterilization.

SUMMARY OF THE INVENTION

An adaptor for delivering antimicrobial fluid to an article to be sterilized comprises an axially elongate body having an interior wall and an exterior wall, being open at a first end, an aperture in the body, where the article to be sterilized contacts the aperture at a contact area, and means for enhancing penetration of the antimicrobial fluid to the contact area. Preferably, the adaptor also comprises a truncated cone sealed to the interior wall of the body.

In accordance with one aspect of the invention, the means for enhancing penetration of the antimicrobial fluid to the contact area can comprise textured or uneven surfaces on the surface surrounding the aperture. Alternatively, the means for enhancing penetration of the antimicrobial fluid to the contact area can comprise a material, at least in the contact area, which is permeable to the antimicrobial fluid. In another embodiment, the adaptor can be formed from a material, at least in the contact area, which has minimal chemical and physical interaction with the antimicrobial fluid. The adaptor according to this invention can be formed using one or a combination of these means for enhancing penetration of the antimicrobial fluid to the contact area.

In accordance with another aspect of the invention, the material of construction of the adaptor, at least in the contact area, can be selected from the group consisting of: thermoplastic polyolefins, including thermoplastic elastomers; fluorovinylidene; chlorovinylidene; liquid crystal polymers, such as wholly aromatic polyester or polyester-amide; silicone rubber; and fluorinated silicone rubber.

In accordance with another aspect of this invention, the inside surface of the aperture is textured or uneven. In accordance with another aspect of the invention, the axially elongate body of the adaptor comprises a cylinder or an elongated body of any cross sectional configuration.

A method of sterilizing a device comprises: connecting the device to an adaptor through an aperture, where the device to be sterilized contacts the aperture at a contact area; placing the device and adaptor into a sterilization chamber; introducing an antimicrobial fluid through the adaptor and device; causing the antimicrobial fluid to penetrate the contact area; and sterilizing the device.

In accordance with another aspect of the invention, the aperture is located in a truncated cone sealed to an interior wall of an axially elongated body, and one end of the axially elongated body is open.

In accordance with another aspect of the invention, the surface of the adaptor surrounding the aperture can be textured or uneven. Alternatively, or in combination, the adaptor, at least in the contact area, can be constructed from a material which is permeable to the antimicrobial fluid. Alternatively, or in combination, the adaptor, at least in the contact area, can be made of a material which has minimal chemical/physical interaction with the antimicrobial fluid.

In accordance with another aspect of the invention, the material of construction of the adaptor, at least in the contact area, can be selected from the group consisting of: thermoplastic polyolefins, including thermoplastic elastomers; fluorovinylidene; chlorovinylidene; liquid crystal polymers, such as wholly aromatic polyester or polyester-amide; silicone rubber; and fluorinated silicone rubber.

In accordance with another aspect of the invention, the antimicrobial fluid is hydrogen peroxide. The device to be sterilized in accordance with one aspect of the invention comprises a lumen. In accordance with another aspect, the device comprises a rod. In accordance with another aspect of the invention, the antimicrobial fluid is additionally introduced into the sterilization chamber. Advantageously, a vessel containing the antimicrobial fluid may be attached to the open end of the axially elongated body of the adaptor.

In accordance with another aspect of this invention, a method for sterilizing a medical device having two or more parts, where there are one or more contact areas between the parts, comprises placing the medical device in a sterilization chamber, introducing an antimicrobial fluid and causing the antimicrobial fluid to penetrate the contact areas, and sterilizing the medical device.

Advantageously, at last one surface on at least one of the parts forming the medical device can have texturing or an uneven surface on the area forming the contact area. Alternatively, or in combination, at least one of the parts can be constructed from a material, at least in the contact area, which is permeable to the antimicrobial fluid. Alternatively, or in combination, at least one part can be made of a material, at least in the contact area, which has minimal chemical/physical interaction with the antimicrobial fluid.

Advantageously, the material of construction of at least one of the parts, at least in the contact area, can be selected from: thermoplastic polyolefins, including thermoplastic elastomers; fluorovinylidene; chlorovinylidene; liquid crystal polymers, such as wholly aromatic polyester or polyesteramide; silicone rubber; and fluorinated silicone rubber.

In accordance with another aspect of this invention, the medical device is a pair of forceps.

DETAILED DESCRIPTION OF THE PREFERRED EMBODIMENT

The method and device of the present invention relates to the sterilization of articles such as medical instruments having a lumen or to any medical instrument having contact surfaces. In addition, the method and device apply to any situation in which an article to be sterilized is in contact with an external housing or other device where there are points of contact between the external housing and the article. Finally, the method applies to medical devices having two or more parts, where there are points of contact between the two parts. Each of these embodiments will be discussed in turn. The terms "sterilize, sterilant", and other forms of this word throughout the specification and claims are to be construed broadly and to include disinfection and other antimicrobial processes.

The first embodiment of the present invention is for the sterilization of lumens or medical instruments having one or more lumens. The term instruments having one or more lumens as used herein applies to medical or surgical devices such as endoscopes, catheters, tubing, or similar instruments or articles having one or more internal lumens. In this embodiment of the device and method of the present invention, antimicrobial fluid may be supplied directly to the lumen or interior of the tube of the instrument during the sterilization process. In general, the lumen is held by an adaptor which is connected to a source of antimicrobial agent. There are contact surfaces between the adaptor and the lumen.

To enhance the sterilization of the contact surfaces, one or a combination of the following properties may be utilized in the adaptor or connector design or material selection: first, applying texture or uneven surfaces to the contact area so as to reduce surface contact and enhance axial diffusion of sterilant; second, constructing the adaptor or connector, at least in the contact area, from a material which has minimal chemical and physical interaction with the sterilant; and third, using a material of construction, at least in the contact area, which is permeable to the sterilant so that the sterilizing agent can penetrate the material, thereby enhancing radial diffusion of the sterilant.

Figure 1:
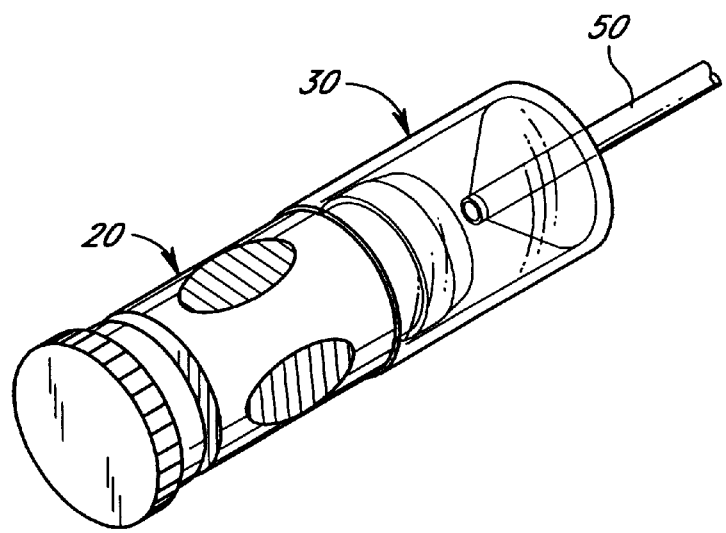
FIG. 1 is a perspective drawing of an assembled booster and adaptor with a lumen inserted in the opening of the adaptor.
Figure 2:
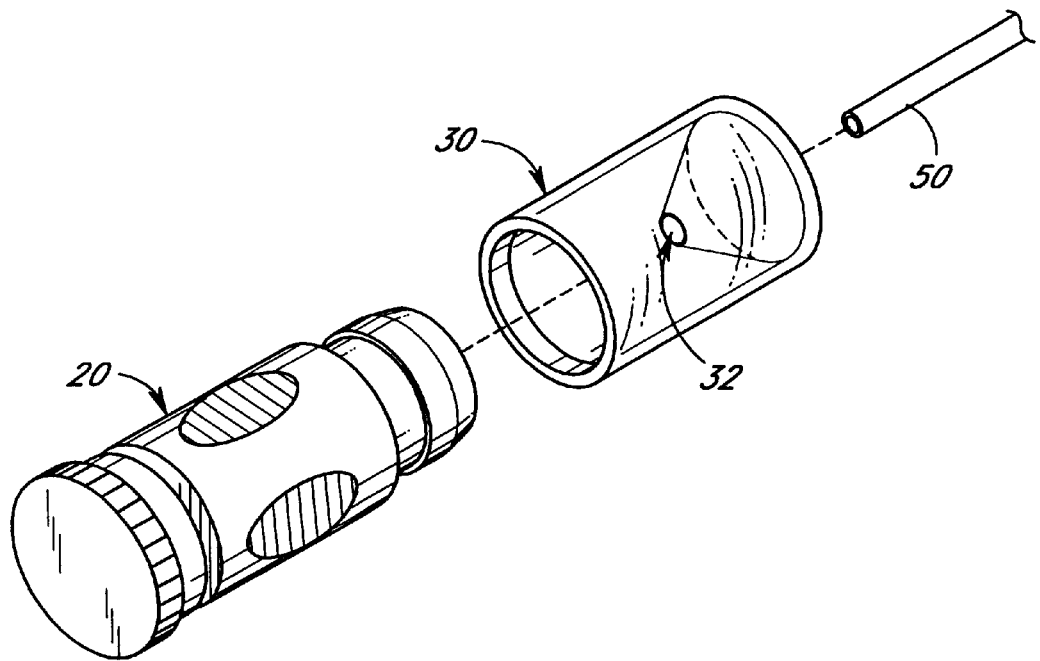
FIG. 2 is an exploded perspective drawing of the booster, adaptor, and lumen.

FIGS. 1 and 2 illustrate a form of apparatus suitable for use in this embodiment. FIG. 1 shows the assembled apparatus, and FIG. 2 is an exploded view, showing the various parts of the apparatus. A booster 20 is attached to an adaptor 30. A lumen 50 is inserted into an opening 32 of the adaptor 30. The opening 32 is normally of slightly smaller diameter than the outer diameter of the lumen 50 so that there is a snug fit between the inside of the opening 32 and the outside of the lumen 50.

Two forms of the booster 20 are described in detail in U.S. Pat. No. 5,580,530 in col. 9 line 11 to col. 12, line 19 and FIGS. 5 to 13, herein incorporated by reference. Briefly, the booster 20 comprises a vessel for containing hydrogen peroxide, a membrane wall capping the vessel containing the hydrogen peroxide, and an opener with a hollow spike which is used to breach the membrane wall to activate the booster so that the hydrogen peroxide can escape from the vessel. One form of the booster is shown as 100 on FIGS. 5 to 9 and an alternative form as 200 on FIGS. 10 and 11 of U.S. Pat. No. 5,580,530.

Figure 3A:
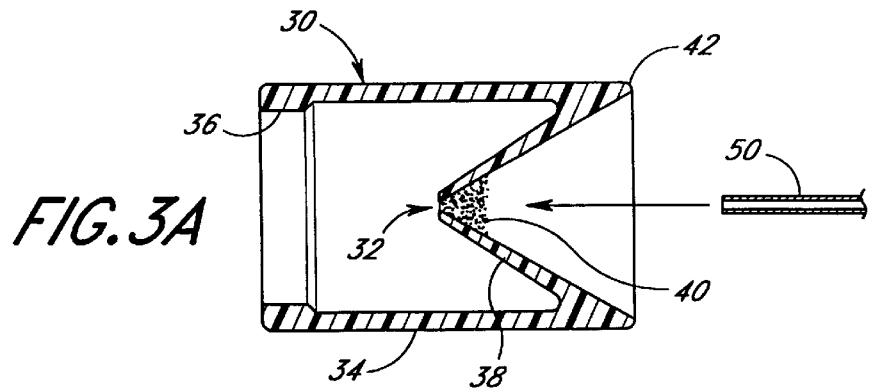
FIG. 3A is a sectional view of the adaptor and lumen, showing how the lumen fits into the opening of the adaptor.

The adaptor 30 is shown in more detail in FIG. 3A herein. The adaptor 30 comprises a cylindrical tubular body 34, an inwardly facing annular flange 36 for firmly attaching the cylindrical tubular body 34 to the booster 20, a truncated cone 38, the opening 32, and texturing 40 on the outer surface of the truncated cone 38 surrounding the opening 32. The adaptor has one or a combination of the following properties.

First, texturing can be added to the contact surface. The texturing can take various forms such as ridges, concentric rings, uneven surfaces, projections having equal heights, projections with varying heights, etc. Whatever form of texturing is used, there can be a plurality of the ridges, rings, or projections of equal or varying heights. The height of the texturing varies and is related to the viscosity of the antimicrobial fluid. The height of the texture varies from 0.01 millimeters to 50 millimeters. The height of the texture for an antimicrobial fluid which is a gas will generally be less than for an antimicrobial fluid which is a liquid, because a gas has a lower viscosity than a liquid. Although the height of the texturing can be determined by one skilled in the art, in general, a height of 0.1 millimeter is preferred for an antimicrobial agent which is a gas. The height of the texturing which is preferred for a liquid is normally in the range of 1 to 5 millimeters, depending on the viscosity of the liquid. The texturing also preferably extends to the inside of the opening 32, so that the area directly facing the lumen 50 is textured as well as the outer surface of the truncated cone 38 surrounding the opening 32. The portion of the truncated cone 38 which is textured is in the range of 0.01 to 50 millimeters, radially extending from the edge of the opening 32. The inwardly facing annular flange 36 fits into a shallow annular groove on the booster 20 when the adaptor 30 is fitted into place on the booster, thereby firmly attaching the adaptor 30 to the booster 20. Those of skill in the art will appreciate that the dimensions of the truncated cone 38 and the opening 32 can be varied to accommodate various types of instruments to be sterilized.

Second, the material, at least in the contact area, can have minimum chemical and physical interaction with the sterilant or sterilizing agent. Chemical interaction includes chemical reaction or catalytic decomposition of the sterilant. Physical interaction includes absorption or adsorption of the sterilant by the material. Third, the material, at least in the contact area, can be permeable to the sterilant so that the antimicrobial fluid can penetrate through the material.

Suitable materials for fabricating the adaptor, at least in the contact area, can include, but are not limited to, polyolefins (including thermoplastic elastomers), fluorinated and/or chlorinated polyolefins (including thermoplastic elastomers), fluorovinylidene, chlorovinylidene, liquid crystal polymers such as wholly aromatic polyester or polyesteramide, silicone rubber, or fluorinated silicone rubber. These materials can be mixed with one or more fillers which have minimum chemical/physical interactions with the chemical sterilant. Fillers are usually added to enhance mechanical, electrical, or thermomechanical properties.

The following procedure may be used when sterilizing equipment with the booster 20 and the adaptor 30. An appropriately sized adaptor 30 is selected for the particular lumen 50 or other equipment to be sterilized. The adaptor 30 is attached to the booster 20, and the lumen 50 or other instrument to be sterilized is inserted into the opening 32. The booster 20 is activated, and the hydrogen peroxide or other sterilizing agent is free to enter the adaptor 30 and the interior of the lumen 50 or instrument. In general practice, the activated booster 20, adaptor 30, and lumen 50 are placed into a sterilization chamber, the chamber is sealed, and the chamber is evacuated, preferably to 100 torr or less. An antimicrobial fluid is then injected into the chamber, where it vaporizes and contacts the exposed surface of the equipment. Various factors known to those skilled in the art can be used to enhance sterilization such as heat, plasma, or high frequency radiation.

The hydrogen peroxide or other antimicrobial fluid in the booster 20 volatilizes when the chamber is evacuated and enters the adaptor 30 and the lumen 50, thereby sterilizing the interior of the lumen. The exterior of the lumen is sterilized by the antimicrobial agent which is injected into the chamber.

Figure 3B:
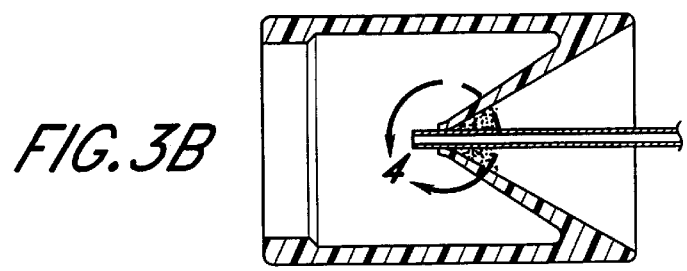
FIG. 3B is a sectional view of the adaptor and lumen, with the lumen inserted into the opening of the adaptor.

FIGS. 3A and 3B illustrate the use of the adaptor 30 with a lumen 50. One skilled in the art can appreciate that the size of the opening 32 on the adaptor can be varied, depending on the size of the lumen or other equipment connected to the adaptor 30. The body of the adaptor can have shapes other than a cylinder, depending on the shape of the booster. For example, a rectangular adaptor would be used if the booster were rectangular. Similar modifications would be obvious to those skilled in the art.

Figure 4:
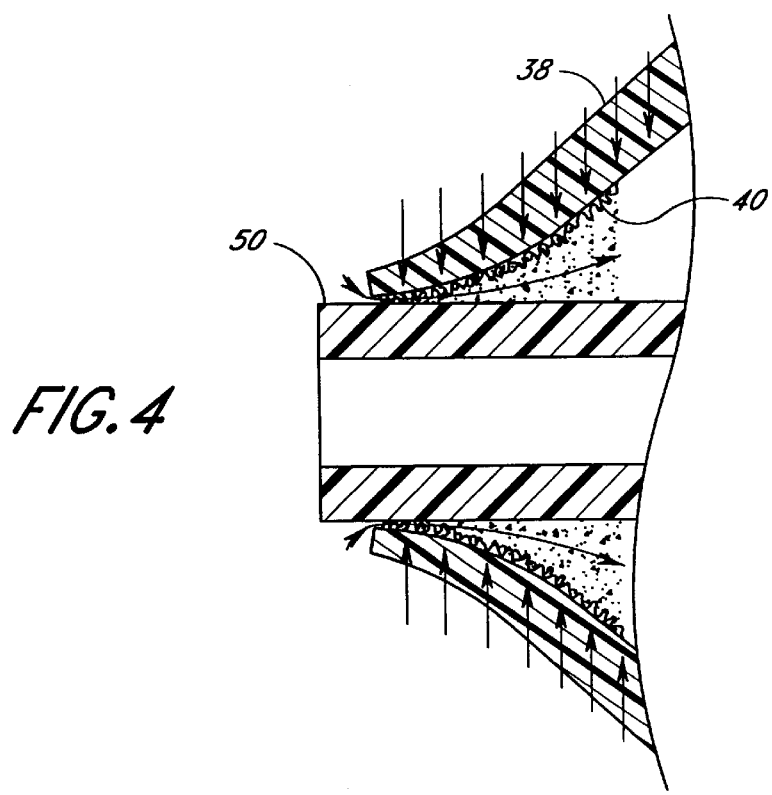
FIG. 4 is a blow-up of FIG. 3B showing a sectional view of the area of contact between the adaptor and the lumen. The flow of the sterilant vapor through the textured area of the adaptor and through the material of the adaptor is shown with arrows.

The adaptor 30 can have several features which make the sterilization of the lumen even more effective than with previous devices. Some of these features are illustrated in FIG. 4, which is a blowup of FIG. 3B, showing the area of contact between the lumen 50 and the adaptor 30. First, the areas of contact between the adaptor 30 and the lumen 50 or other medical device can be reduced by using textured surfaces on the adaptor 30. Thus, the opening 32 and the part of the truncated cone 38 which can contact the lumen 50 can be textured. This is shown on FIG. 4. Only the tips of the texturing devices remain as areas of contact between the adaptor 30 and the lumen 50. This contact area is far less than if the texturing were not present. In addition, there are small gaps between the ridges or "bumps", which create an uneven surface. The antimicrobial agent can enter these gaps and reach areas which would otherwise be inaccessible.

Finally, if the material used to construct the adaptor 30 is permeable to the antimicrobial agent, typically hydrogen peroxide, peracetic acid, or chlorine dioxide, further enhancement of the sterilization effectiveness can be achieved. The antimicrobial agent thus penetrates the adaptor 30 to reach any areas of contact between the adaptor 30 and the lumen 50 or other instrument which remain after these contact areas are minimized through surface texturing. FIG. 4 shows arrows illustrating the penetration of the sterilant vapor to the contact areas both through the gaps between the unevenness of the texturing and through the permeable material from which the adaptor 30 can be fabricated.

The effectiveness of penetration of the antimicrobial agent through the material of the adaptor to the contact areas can be even further enhanced by making the adaptor thinner in the contact areas than in the remainder of the adaptor. For example, in FIGS. 3A and 4, the wall thickness of the truncated cone 38 of the adaptor 30 decreases from the outer end 42 to the opening 32. The portion of the truncated cone 38 which is in contact with the lumen 50 is the thinnest part of the truncated cone, and the antimicrobial agent can penetrate to the contact area between the adaptor and the lumen more effectively than if the adaptor in this area were thicker. Making the adaptor thinner in the contact areas than in the remainder of the adaptor is a way to further enhance the penetration of the antimicrobial agent through the material of the adaptor into the contact area Although this is a preferred embodiment, it is not a required feature.

By using one or a combination of these features in the adaptor 30, the antimicrobial agent can penetrate the areas of contact between the adaptor 30 and the lumen 50 more effectively than in previous designs. These features include: applying texture or uneven surfaces to the contact area so as to reduce surface contact and enhance bidirectional diffusion of sterilant; using a material which has minimal chemical and physical interaction with the sterilant; and forming the adaptor from a material that is permeable to the sterilant so that the sterilizing agent can penetrate the material.

The methods of the present invention can be used whenever there are areas of contact between an article to be sterilized through sterilization and a connecting device for the article. Often, the connecting device will have an aperture through which the article is inserted. There are areas of contact between the aperture of the connecting device and the article to be sterilized. The article to be sterilized can comprise a lumen, rod, or other device. The methods of the present invention can be used in the connecting device and/or the article to be sterilized. These methods include the use of texturing on the areas of the connecting device which contact the device to be sterilized in order to reduce the contact area between the article and the connecting device. Second, the connecting device can be made of a material which is permeable to the antimicrobial agent so that any remaining contact surfaces can be sterilized by penetration of the antimicrobial agent through the material of the adaptor. Third, the selected material can be a material which has minimal physical and chemical interaction with the antimicrobial agent. Ways to optimize these design modifications will be apparent to those skilled in the art.

These methods can also be used to enhance the penetration of antimicrobial agent to contact areas within a medical device. Often a medical device is made of two or more pieces. There are likely to be contact areas between the pieces from which the medical device is formed. One example of a medical device made up of two or more pieces and having contact areas is a pair of forceps. The methods of the present invention can be used to enhance the penetration of the antimicrobial agent to these contact areas.

One or more of the pieces forming the medical device can incorporate the features of the present invention to enhance the penetration of the antimicrobial agent to the contact areas. These features include the use of texturing or uneven surfaces on one or more of the pieces forming the medical device in the contact areas between the two or more pieces. The texturing will help to reduce the contact area. Second, one or more of the pieces forming the medical device, at least in the contact area, can be made of a material which is permeable to the antimicrobial agent. Third, the material selected to form one or more of the pieces forming the medical device, at least in the contact area, can be a material which has minimal physical and chemical interaction with the antimicrobial agent. Any one or a combination of these features can be used to enhance the penetration of the antimicrobial agent to the contact areas between the two or more pieces forming a medical device.

The antimicrobials used with the methods and devices of the various embodiments of the present invention include solutions of glutaraldehyde, hydrogen peroxide, chlorine dioxide, peracetic acid, or other antimicrobials in an inert medium. Although high concentrations of the antimicrobial agents are more effective, material compatibility and handling problems may arise at high concentrations.

Various modifications and alterations of this invention will be apparent to those skilled in the art without departing from the scope and spirit of this invention. It should be understood that the invention is not limited to the embodiments disclosed therein, and that the claims should be interpreted as broadly as the prior art allows.

What is claimed is:

1. An adaptor for delivering antimicrobial vapor or gas to an article to be sterilized, said adaptor comprising:
   an axially elongate body made of a material having an interior wall and an exterior wall, and being open at a first end thereof; and
   an aperture in said body, wherein said article to be sterilized contacts said aperture at a contact area, wherein said body is textured with projections in the entire contact area, wherein said projections and said material are adapted such that when antimicrobial vapor or gas is applied thereto, more antimicrobial vapor or gas flows around said projections than through the material of the body of said adaptor.

2. The adaptor of claim 1, further comprising a truncated cone sealed to the interior wall of said body.

3. The adaptor of claim 1, further comprising textured or uneven surfaces on a surface of said body surrounding said aperture.

4. The adaptor of claim 1, wherein the material, at least the material in said contact area, is permeable to an antimicrobial fluid.

5. The adaptor of claim 1, wherein the material, at least the material in the contact area, has minimal chemical and physical interaction with an antimicrobial fluid.

6. The adaptor of claim 1, wherein the material, at least the material in the contact area, is selected from the group consisting of: thermoplastic polyolefins, including thermoplastic elastomers; fluorinated and/or chlorinated polyolefins, including thermoplastic elastomers; fluorovinylidene; chlorovinylidene; liquid crystal polymers, such as wholly aromatic polyester or polyester-amide; silicone rubber; and fluorinated silicone rubber.

7. The adaptor of claim 1, wherein the inside surface of said aperture is textured with projections or uneven.

8. The adaptor of claim 1, wherein said axially elongate body comprises a cylinder.

9. A method of sterilizing a device comprising the steps of:
   connecting said device to an adaptor through an aperture, wherein the device to be sterilized contacts said aperture at a contact area, wherein said adaptor is made from a material and wherein the adaptor is textured with projections in the entire contact area;
   placing said device and adaptor in a sterilization chamber;
   introducing an antimicrobial vapor or gas through said adaptor and device; wherein said projections and said material are adapted such that when antimicrobial vapor or gas is applied thereto, more of said antimicrobial vapor or gas flows around said projections than through the material of said adaptor; and sterilizing said device.

10. The method of claim 9, wherein said aperture is located in a truncated cone sealed to an interior wall of an axially elongated body, and wherein a first end of said axially elongated body is open.

11. The method of claim 10, wherein a vessel containing an antimicrobial fluid is attached to said first end of said axially elongated body.

12. The method of claim 9, wherein the material, at least the material in the contact area, is permeable to an antimicrobial fluid.

13. The method of claim 9, wherein the material, at least the material in the contact area, has minimal chemical/physical interaction with an antimicrobial fluid.

14. The method of claim 9, wherein the material, at least the material in the contact area, is selected from the group consisting of:
   thermoplastic polyolefins, including thermoplastic elastomers; fluorinated and/or chlorinated polyolefins, including thermoplastic elastomers; fluorovinylidene; chlorovinylidene; liquid crystal polymers, such as wholly aromatic polyester or polyester-amide; silicone rubber; and fluorinated silicone rubber.

15. The method of claim 9, wherein said antimicrobial vapor or gas is hydrogen peroxide.

16. The method of claim 9, wherein said device comprises a lumen.

17. The method of claim 9, wherein said device comprises a rod.

18. The method of claim 9, wherein the introducing step additionally comprises introducing an antimicrobial fluid into said sterilization chamber.

19. A method of sterilizing a medical device having at least two parts, wherein there is at least one contact area between the at least two parts and wherein said at least one contact area is made of at least one material, comprising the steps of:
   providing a plurality of projections on the entire at least one contact area;
   placing said medical device in a sterilization chamber;

introducing an antimicrobial vapor or gas into said sterilization chamber, wherein said projections and said at least one material are adapted such that more antimicrobial vapor or gas flows around said projections than through said at least one material; and sterilizing said medical device.

20. The method of claim 19, wherein at least one of the at least two parts of said medical device is constructed, at least in the contact area, from a material which is permeable to an antimicrobial fluid.

21. The method of claim 19, wherein at least one of the at least two parts of said medical device is made, at least in the contact area, of a material which has minimal chemical/physical interaction with an antimicrobial fluid.

22. The method of claim 19, wherein the material of construction of at least one of the at least two parts of said medical device is selected, at least in the contact area, from the group consisting of;

thermoplastic polyolefins, including thermoplastic elastomers; fluorinated and/or chlorinated polyolefins, including thermoplastic elastomers; fluorovinylidene; chlorovinylidene; liquid crystal polymers, such as wholly aromatic polyester or polyester-amide; silicone rubber; and fluorinated silicone rubber.

23. The method of claim 19, wherein said antimicrobial fluid is hydrogen peroxide.

24. The method of claim 19, wherein said medical device is a pair of forceps.

* * * * *